United States Patent
Frison et al.

(10) Patent No.: US 9,339,179 B2
(45) Date of Patent: May 17, 2016

(54) CORNEAL CONFOCAL MICROSCOPE

(75) Inventors: Renato Frison, Chions (IT); Cesare Tanassi, Susegana (IT); Walter Zanette, San Fior (IT)

(73) Assignee: Sifi Medtech S.R.L., Aci Sant'Antonio (IT)

( * ) Notice: Subject to any disclaimer, the term of this patent is extended or adjusted under 35 U.S.C. 154(b) by 475 days.

(21) Appl. No.: 13/876,539

(22) PCT Filed: Sep. 28, 2011

(86) PCT No.: PCT/EP2011/066870
§ 371 (c)(1),
(2), (4) Date: Jul. 16, 2013

(87) PCT Pub. No.: WO2012/041909
PCT Pub. Date: Apr. 5, 2012

(65) Prior Publication Data
US 2013/0293841 A1    Nov. 7, 2013

Related U.S. Application Data

(60) Provisional application No. 61/387,387, filed on Sep. 28, 2010.

(51) Int. Cl.
*A61B 3/10* (2006.01)
*G02B 21/00* (2006.01)

(52) U.S. Cl.
CPC .......... *A61B 3/1025* (2013.01); *G02B 21/0024* (2013.01); *G02B 21/0028* (2013.01); *G02B 21/0032* (2013.01)

(58) Field of Classification Search
CPC ................ A61B 3/1025; A61B 3/10–3/185; G02B 21/0024–21/0084
See application file for complete search history.

(56) References Cited

U.S. PATENT DOCUMENTS

| | | | |
|---|---|---|---|
| 4,734,578 A * | 3/1988 | Horikawa | 250/234 |
| 4,764,005 A * | 8/1988 | Webb et al. | 351/205 |
| 5,177,511 A * | 1/1993 | Feuerstein et al. | 351/205 |
| 5,321,446 A * | 6/1994 | Massig | A61B 3/135 351/214 |
| 6,585,723 B1 * | 7/2003 | Sumiya | 606/5 |
| 2004/0218145 A1 * | 11/2004 | Matsumoto | 351/214 |
| 2007/0030447 A1 | 2/2007 | Yamaguchi et al. | |
| 2007/0258045 A1 | 11/2007 | Yamaguchi et al. | |
| 2007/0291230 A1 | 12/2007 | Yamaguchi et al. | |
| 2007/0291277 A1 | 12/2007 | Everett et al. | |

FOREIGN PATENT DOCUMENTS

| | | |
|---|---|---|
| EP | 0620468 A1 | 10/1994 |
| WO | 2010083381 A1 | 7/2010 |
| WO | WO 2010113193 A1 * | 10/2010 |

OTHER PUBLICATIONS

Schmid, Gregor F., "Axial and peripheral eye length measured with optical low coherence reflectometry" Journal of Biomedical Optics, vol. 8, No. 4 (Oct. 2003), pp. 655-662.*
International Search Report for corresponding PCT International Application No. PCT/EP2011/066870, received at IB Feb. 14, 2012.
Stachs et al., "In vivo three-dimensional confocal laser scanning microscopy of the epithelial nerve structure in the human cornea," Graefes Arch Clin Exp Ophthalmol, 245(4):569-75 (Mar. 20, 2007).

* cited by examiner

*Primary Examiner* — Thomas K Pham
*Assistant Examiner* — Cara Rakowski
(74) *Attorney, Agent, or Firm* — LeClairRyan, a Professional Corporation

(57) ABSTRACT

A corneal confocal microscope characterized by a particular illumination system.

10 Claims, 11 Drawing Sheets

The CCM full optical path

FIG. 1E

FIG. 2 – The CCM full optical path

FIG. 3 – The CCM Ring Light Illumination path

FIG. 4 – The CCM Imaging path

FIG. 5 – The CCM Imaging path in non-confocal mode

FIG. 6 – The CCM Fixation Target path

FIG. 7A – Operator Side

Fig. 7B – Patient side

Fig. 7C - Side View

FIG. 7E - Patient side with rotated touch screen

Fig. 7D - Rendering

FIG 8A – epithelial cells

FIG. 8B – Basal layer

FIG. 8C – Endothelial cells

FIG. 9 - The Schematic Diagram of the system

FIG. 10

CORNEAL CONFOCAL MICROSCOPE

This application is a national stage application under 35 U.S.C. §371 of PCT Application No. PCT/EP2011/068870, filed Sep. 28, 2011, which claims the priority benefit of U.S. Provisional Patent Application Ser. No. 61/387,387, filed Sep. 28, 2010, both of which are hereby incorporated by reference in their entirety.

FIELD OF THE INVENTION

The present invention provides a novel method and system for confocal microscope illumination.

PRIOR ART

A major improvement for the biomicroscopy of the human eye became reality with the advent of the in-vivo three-dimensional confocal microscopy. Leeuwenhoek's single lens microscope was the first instrument developed to investigate the human eye structures, followed by the ophthalmoscope, the slit lamp, and the specular microscope. The confocal microscopy of the living eye delivers high contrast optical sections that theoretically allow for reconstructing three-dimensional volume images of ocular tissues. For example, confocal microscopy can deliver three-dimensional volume images of a cornea, a crystalline lens, a retina, as well as other structures in the eye.

Confocal microscopy allows new diagnostic techniques that produce high resolution cellular imaging for a more complete description and correlation of ocular pathologies and disorders. With regard to optical instruments, an objective (optical objective or microscope objective) is an optical element that gathers light from the observed object and produces a real image by focusing the light. Examples of objectives include single or multiple lenses and/or mirrors, or combinations of several optical elements.

A typical confocal microscope consists of two conjugated (confocal) apertures that allow to get rid of the light that is not in the focal plane of the microscope objective. The same objective that projects the light, is also used to collect both scattered and reflected light from the same focal plane into a charge coupled device (CCD), that forms the final image. In order to form a complete two-dimensional optical section, the microscope's illumination is scanned over the whole focal plane at a very high speed. An entire scan must be completed in at least 1/30 of second in order to avoid eye motion and other motion related artifacts. Motion of the eye and/or body presents additional difficulties for a typical confocalmicroscope when reconstructing a volumetric image of a cornea. For example, in order to create enough optical sections for a volume reconstruction, a typical volume reconstruction requires a large number of images (e.g., anywhere around 200 to 300 images). The acquisition of these images can take several seconds (e.g., between 5 and 10 seconds). However, the eye undergoes near continuous motility due to eye movement resulting in spatial motion or X/Y motion, or as well tidal motion of the body, such as the motion caused by heartbeat or breathing resulting in (focal plane motion or Z motion). Due to the movement of the eye that occurs during image acquisition, many if not all of the optical images are collected with a non accurate volume reference to a single coordinate system (XYZ origin). This discrepancy can make it almost impossible to reconstruct a volumetric image that can be safely used for quantitative measurements (like pachimetry, layer positions for Lasik surgery, or volumetric cell counting). In addition, due to the scanning light, which appears at the patient as a flickering light, it can be very difficult for a patient to maintain a stable fixation point. The inability to maintain a stable fixation point can cause additional motion artifacts and misplacement of the optical section images. All the existing solutions on the market offer a limited answer to this issue providing an external fixation light.

A product manufactured by Nidek, Inc. attempts to address the above issues by using an applanating device, called Z-ring that acts as an encoder and as a stabilizer during the examination of the eye. However, one drawback is that one main advantage of a confocal microscope, is that the microscope is non-invasive. The use of an applanating structure becomes somewhat invasive. Moreover, performing an examinaton during applanating the eye cause observation of structures in a non-physiological status. This produces additional artifacts (e.g., folds). Also, many aged patients do not tolerate the invasive procedure well. Furthermore, contact with a device raises a concern about the possibility of causing scratches on a patient's cornea.

The Nidek confocal device consists of an illumination moving slit conjugated to a plane in the corneal layer being examined and an imaging moving slit conjugated to the same tissue plane. The second slit receives the light from the eye section to be imaged and filters out the reflected light from unfocused tissue layers. The combination of the illumination and imaging optical path is realized through a beam splitter consisting of two mirrors perpendicular to one another and placed close to the objective lens: one mirror reflects the light coming from the illumination path on one half of the objective microscope entrance pupil; the second one receives the light back scattered by the examined layer and transmits it into the imaging path to a CCD. Both slits are moved synchronously to scan a small portion of tissue and create a full field of view magnified image of the structures being analyzed.

Another device, manufactured by Tomey Corporation, utilizes a slit scanning system in order to collect images of the corneal tissue layers. In this design two indipendetly slits are located in conjugated planes and moved synchronously to produce the optical sectioning in real time. The use of slit illumination compared to pinhole illumination has the advantage of decreasing the scan time thus improving the patient comfort.

Another product manufactured by Heidelberg Engineering, Heidelberg Retinal Tomography (HRT), utilizes a scanning diode laser to illuminate and acquire images of the examined section of the eye by focusing a single point in the image. The emitted beam is directed in the x and y directions of the image plane by means of oscillating mirrors and a luminance detectors measures the light reflected from each point in the image after passing through a confocal imaging aperture.

The depth of the focal plane is automatically adjusted by shifting the confocal aperture to collect multiple images of the examine tissue in order to create a 3 dimensional representation.

Moreover, Heidelber Engineering proposes a cornea module that can be equipped into the HRT instrument delivering corneal optical sections with a laser scanning system. Again the system applanates the eye. Even though there may be less pain than using the Z-ring, there is a concern regarding the possibility to cause surface scratches on the patient's cornea. In view of the above, there remains a need for an improved device.

Figure 1:
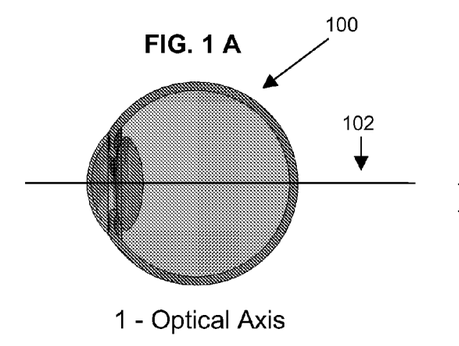
FIGS. 1A to 1D illustrate axes of the eye.
FIG. 1E shows an example for aperture distribution.

A brief discussion of the axes of the eye is helpful to understand the proper eye alignment and the benefits of a proper alignment during the eye examination. As shown in FIG. 1A, an imaginary line passing through the centers of curvature of the optical surfaces in a least squares sense is taken as the optical axis 102 of the eye 100. In general the optical axis 102 is ill-defined due to the complex shapes of the various ocular surfaces. As shown in FIG. 1B, a visual Axis 104 connects the fixation point to the front nodal point and the back nodal point to the fovea 106. The angle between axis 102 and axis 104 is usually denoted by angle α and ranges between $4° < α < 8°$. The pupillary axis, FIG. 1C, strikes the cornea at right angles and passes through the center of the entrance of tile pupil. Finally, as shown in FIG. 1D, a line of sight (LOS) connects a fixation point to the center of the entrance pupil and the center of the exit pupil to the fovea. The LOS is equivalent to the chief ray from the fixation point. The line of sight, with angle K from the pupil axis, typically has $K ≤ α$ (D6-4).

SUMMARY OF THE INVENTION

The present invention provides a novel method and system for confocal microscope illumination. The measuring method uses a drilled mirror that projects a beam of rays onto a section of the cornea tissue through a cone of light: the light coming from the illumination path of the device passes through the light cone outer region while the light back scattered by the corneal layers is collected through the light cone inner region. This illumination system reduces the light reflected back by the anterior surface of the cornea into the imaging path and improves image contrast.

Furthermore, the drilled mirror is conjugated to the entrance pupil of the microscope objective lens by means of an optical relay system which provides full field images without vignetting.

DETAILED DESCRIPTION OF THE INVENTION

In the following detailed description of the preferred embodiment reference is made to the accompanying drawings which form a part hereof, and in which it is shown by way of illustration specific embodiments in which the invention mat be practiced. It is understood that other embodiments may be utilized and structural changes may be made without departing from the scope of the preferred embodiment of the present invention.

In some embodiments a set of optical sections of the corneal tissue is captured by further image capturing means; the relative position of each image is determined after positioning the illumination slit on the outer surface of the cornea.

In some embodiments the novel method and system allow for reducing an amount of reflected light into an image path. In other embodiments additional variations can also increase the efficiency and sensitivity of the instruments by reducing the amount of light energy that is needed to acquire optical sections.

In some embodiments the systems and methods described include an optical path design that include an optical low coherence reflectometry (OLCR) distance meter that is coaxially arranged into the system in order to physically encode all the acquired optical section positions. This feature enables the system to "map", with absolute coordinates, all acquired optical sections into the three-dimensional space.

Due to the reduced light energy required by the system, within the same optical path, it's now possible to host an internal fixation target that is easily visible. This internal fixation target assists in allowing all patients to maintain their fixation during the examination. One benefit of such a feature is to reduce spatial motion artifacts into the acquired optical sections or images.

The fixation target optical assembly can also be used to project an alignment pattern into the examined eye corneal plane. This alignment pattern allows the system to automatically approach the patient eye. In order to perform initial alignment, the confocal imaging is temporarily disabled by sliding a specific optical path that skips the confocal aperture.

The systems and methods described herein allow for capturing accurate histological samples of an in-vivo examined cornea. The images allow for reconstructing and rendering an accurate volumetric model of the examined cornea. Variations also allow for 2 and 3 dimensional measurements of the target cornea as well as pachimetry and morphology and density indexes for various layers of the examined cornea.

The constructed model data can assist physicians, surgeons, and other medical practitioners in pre-operative assessments and in follow-up evaluation of medical treatments.

Furthermore, variations of the system allow for increased repeatability of an eye examination due in part to little or minimal user intervention during the exam. In additional variations, the user interface and the ergonomics of the system assist in increasing the improved results. For example, variations including a rotatable touch screen monitor allow operation of the system from the front side or operator side as well as from the patient side (e.g., over the patient's shoulder). The latter being very useful to patients requiring assistance during examinations (e.g., disabled, children, elderly, etc . . . ).

Figure 2:
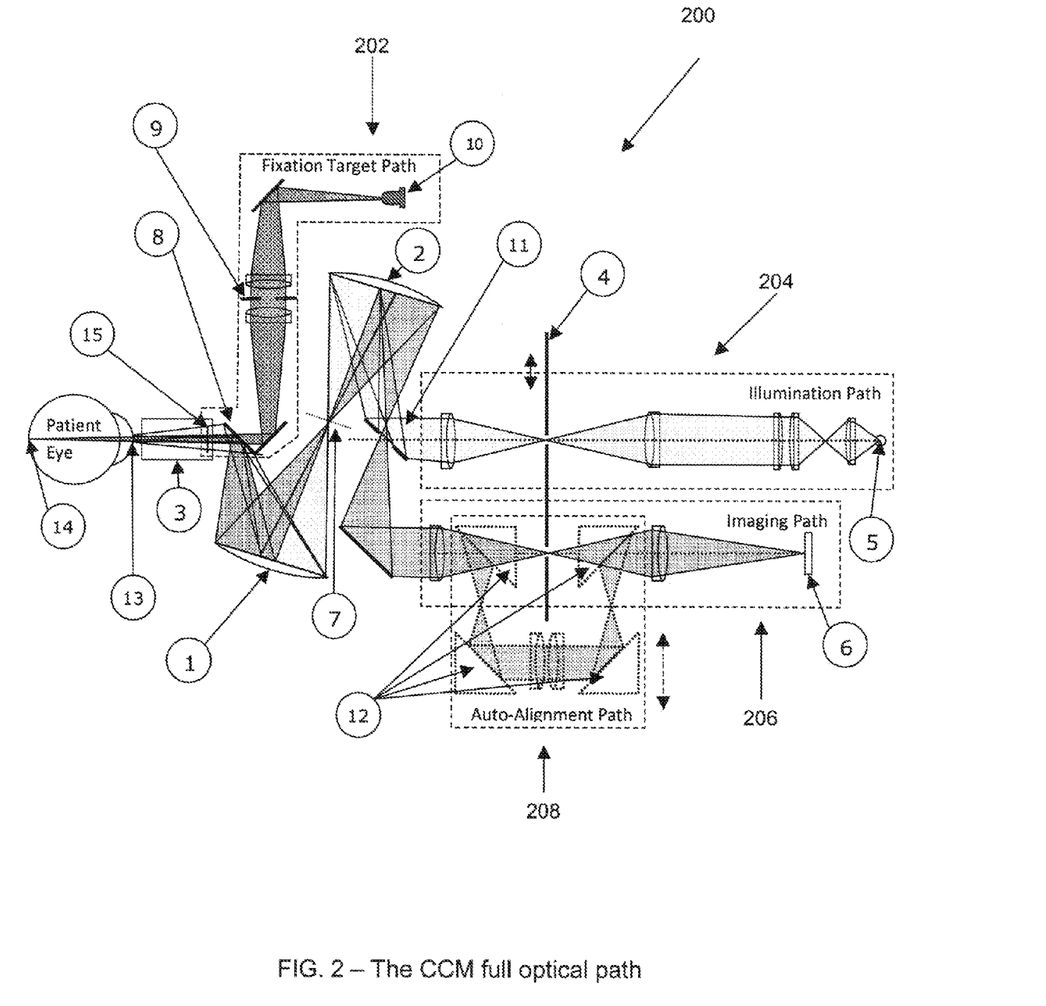
FIG. 2 shows a representation of an example of a corneal confocal microscope.

One variation of the system according to the present disclosure is found in FIG. 2.

As shown, the system is formed by a 3-Axis mechanical assembly equipped with an optical workbench, coaxially assembled with the main optical axis that allows to obtain optical sections of the eye cornea.

The mechanics is driven by an automatic alignment system, that drives the microscope lens until it overlaps with the examined eye optical axis.

The main optical component of the confocal microscope described herein is a long working distance microscope objective lens. In this example, the eye of the patient need not to be placed in direct contact with the objective lens itself and this improves the patient comfort during the medical examination.

Figure 10:
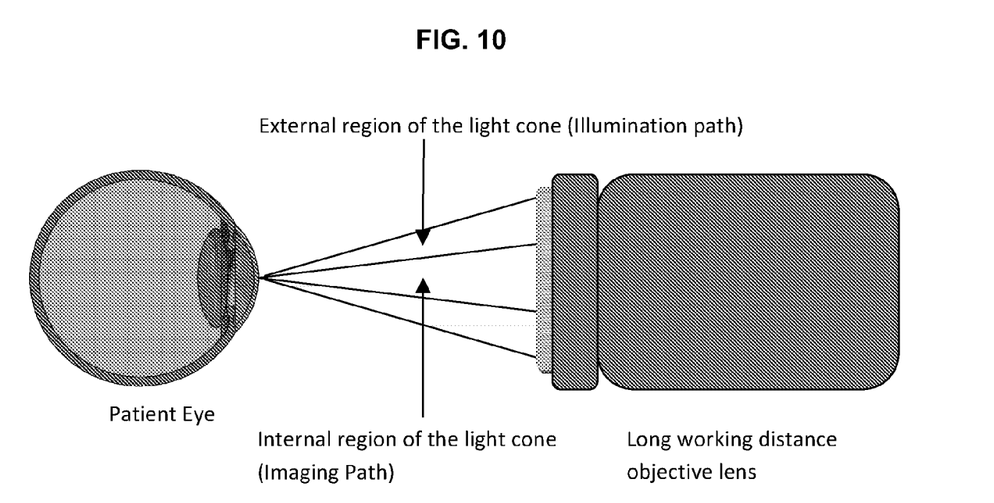
FIG. 10 provides s scheme of the relative positions of patient eye and long working distance objective lens

Additionally, the corneal confocal microscope is built upon an annular illumination system that may generally comprise a drilled mirror which directs the light, e.g., from an LED light source, conjugated to the entrance of the pupil of the microscope objective lens. In this way a light cone exits from the objective lens (FIG. 10) and impinges on the corneal surface. The light coming from the illumination path travels through the outer volume of the light cone while the inner volume is filled with the light back scattered by the corneal tissue being examined The light reflected back by the corneal surface is gathered by the same objective lens and sent to the hole of the aforementioned drilled mirror which behaves like a beamsplitter. By passing through the mirror hole, the light entering the imaging path meets a small aperture (e.g., a pinhole or a slit). A slit aperture is typically the most common solution used in corneal confocal microscopes. The aperture is conjugated to another identical aperture laid on the same plane but positioned on the illumination path. In this way, the confocal principle requirements are fulfilled and the rendering of the corneal layers provided.

Unlike other approaches (where the splitting and recombining of the illumination and imaging light paths are obtained by utilizing two plane mirrors tilted 45° with respect to the optical axis of the objective lens), the drilled mirror solution corrects image artifacts due to light vignetting. Moreover, the light reflected back by the anterior corneal surface impinges only on the outer surface of the drilled mirror and thus, being re-directed to the illumination path, does not enter the imaging path. This highly reduces image artifacts due to light-back reflection which are known to be a major drawback limiting the use of long working distance objectives in confocal microscopes specifically designed for the corneal imaging and improves image contrast.

The drilled mirror is conjugated to the entrance pupil of the objective lens by means of a unit magnification relay lens system. One possible emdobiment of this relay system can be implemented by using two spherical mirrors of suitable and equal focal length. This may prove to be effective in removing annoying ghost reflections which typically decreases image quality.

In corneal confocal microscopes, a single rectangular aperture or slit (e.g., 80/160 or 240 µm width and an height that can fill the whole field of view) both in the imaging and the illumination path may be used.

The cornea can be illuminated also by multiple apertures (e.g., pinholes or slits) which may be evenly spaced out over the whole field of view in one embodiment and have a width which is comparable or even smaller than the single aperture width. In this manner, the multiple aperture configuration may increase the image brightness due to a higher flux of light impinging on the cornea. Alternatively, a dimmer light source may be utilized which does not reduce the image contrast.

Figure 1E:
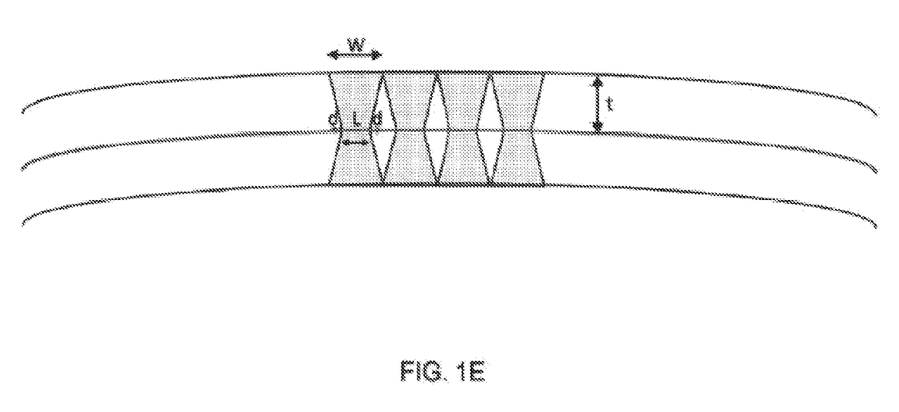

One method to estimate the total number of multiple apertures that can be placed in the confocal plane is given by equation (1). Each slit is projected over the focus plane through a beam of rays which defines a cone of light; these cones may be prevented from overlapping one another inside the corneal layer delimited by the thickness, t, as shown in FIG. 1E. The width, W, of the cone at a distance t from the focal plane is given by the sum of the slit amplitude, L, in the focal plane and the aperture due to the light cone numerical aperture 2d at a distance t. The angle, α is the angle inside the cornea given by the numerical aperture of the objective lens.

$$W = 2d + L = 2t\mathrm{Tan}[\alpha] + L \quad (1)$$

$$N_{slit} = \frac{\text{Field of View}}{VW} \quad (2)$$

By knowing the slit width aperture W at a distance t from the focal plane, the total number of slits that can be utilized in the available field of view without overlapping can be easily obtained by means of equation (2).

An OLCR distance meter coaxially positioned into the main optical axis detects the distances of the corneal surfaces, thus providing the required information to properly reorder all of the captured optical sections, and get rid of the patient eye motion that usually affects this type of examination. The system also includes a coaxial fixation target system. This system has two different purposes.

First, it projects a deep focus image of an illumination source (e.g., an LED, a red LED, etc.) on the retina of the examined eye. The large depth of focus allows the fixation target to be visible even for large refractive errors of the patient's eye. Second, the system projects an image (e.g., a cross) onto the corneal surface. This image is used by the imaging system to pre-align the optical axis of the confocal microscope with the examined eye's visual axis. When the pre-alignment is accomplished, an additional optical automatic alignment system is inserted into the existing imaging path.

The auto-alignment path, formed by four prisms or mirrors and two achromatic doublets, is shifted into the imaging path to deviate the image into a non-confocal path. Doing so the system may look at a conventional image of the front part of the examined eye. The projection system provides the necessary information to drive the 3-Axis mechanical assembly to position the microscope at the apex of the examined eye and then the examination starts.

FIG. 2 shows a schematic example of the basic details of the embodiment described herein and illustrates the overall scheme of the optical path. As illustrated, the system can include four main sections, the fixation target path 202, a ring illumination path 204, an imaging path 206, and an auto-alignment path 208 plus at least two spherical mirrors I and 2 used as a pupil re-imager.

Figure 3:
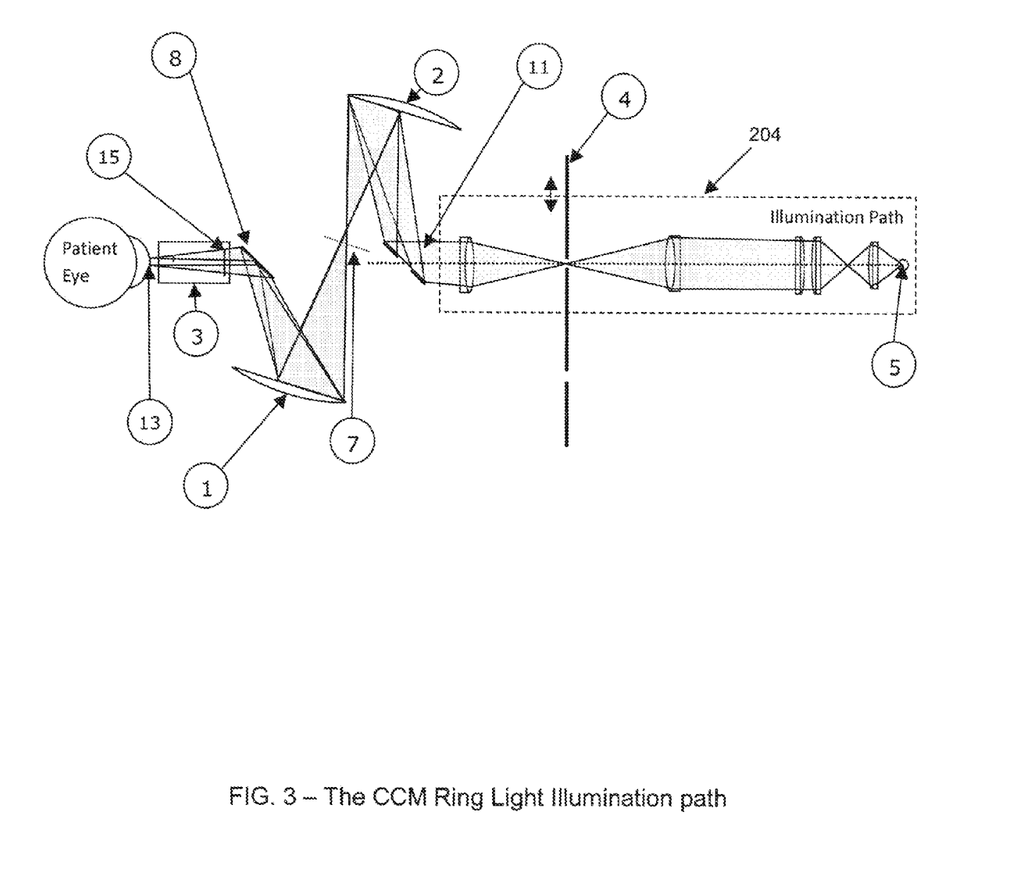
FIG. 3 illustrates a detailed view of an illumination path of the corneal confocal microscope system.
Figure 4:
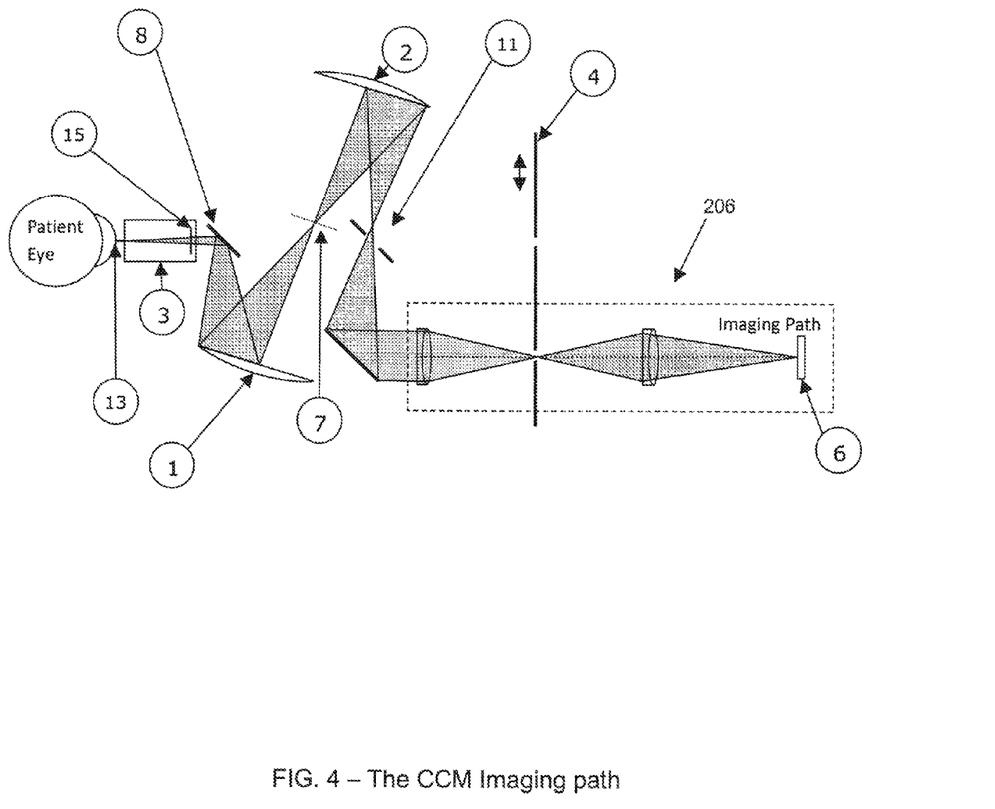
FIG. 4 shows a detailed view of an imaging path of the corneal confocal microscope system.

FIG. 3 illustrates the ring illumination path 204 that starts at a light source (with a blue wavelength, for istance) 5 and passes through a scanning slit 4 and to a drilled mirror II. After the first spherical mirror 2, the light creates an image of the slit on an intermediate image plane 7, then the light hits a second spherical mirror I and a blue reflective coated beam splitter 8 to form a ring light image at the entrance pupil of an objective lens 15. Finally, the objective lens 3 focuses the scanning light onto the focal plane of the subject eye 13 being examined FIG. 4 shows a layout of the imaging path 206. The imaging path starts from subject's corneal focus plane 13 and passes through the pupil of the objective lens 15. After being reflected by the blue reflective coated beam splitter 8, the light impinges on a first spherical mirror 3, and forms an image on intermediate image plane 7. Then, the image is transferred by the second spherical mirror 2, to the drilled mirror 11 and the scanning slit 4 up to the CCD camera 6 where the image is formed and captured.

Figure 5:
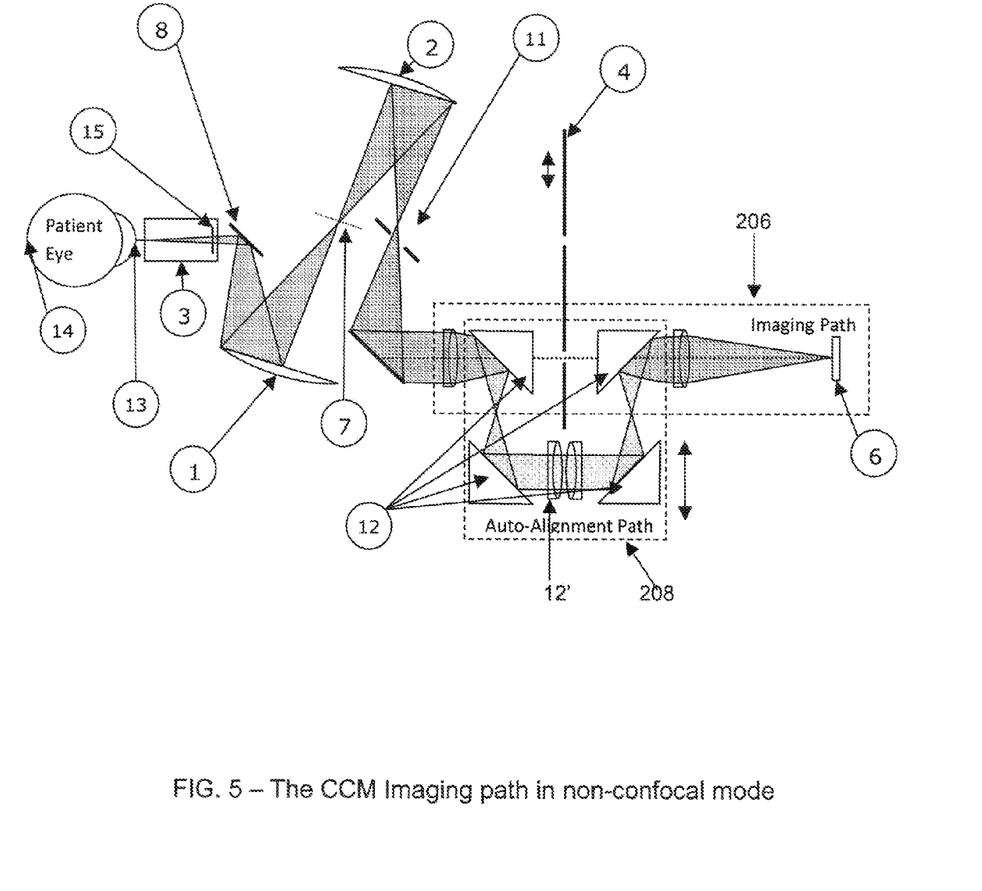
FIG. 5 shows a detailed view of an imaging path of the corneal confocal 25 microscope system when in non-confocal mode.

FIG. 5 illustrates a schematic of an imaging path 206 in a non-confocal mode. During the preliminary alignment of the instrument it is necessary to look at a macro image of the front part of the cornea. For this reason the auto-alignment path 208, that consists of an assembly of prisms 12 and achromatic lenses 12', is shifted into the imaging path 206 to remove confocality of the acquired images. Thus the system, in this specific condition, can see the target mires (D6-9) projected onto the corneal surface for a proper positioning.

Figure 6:
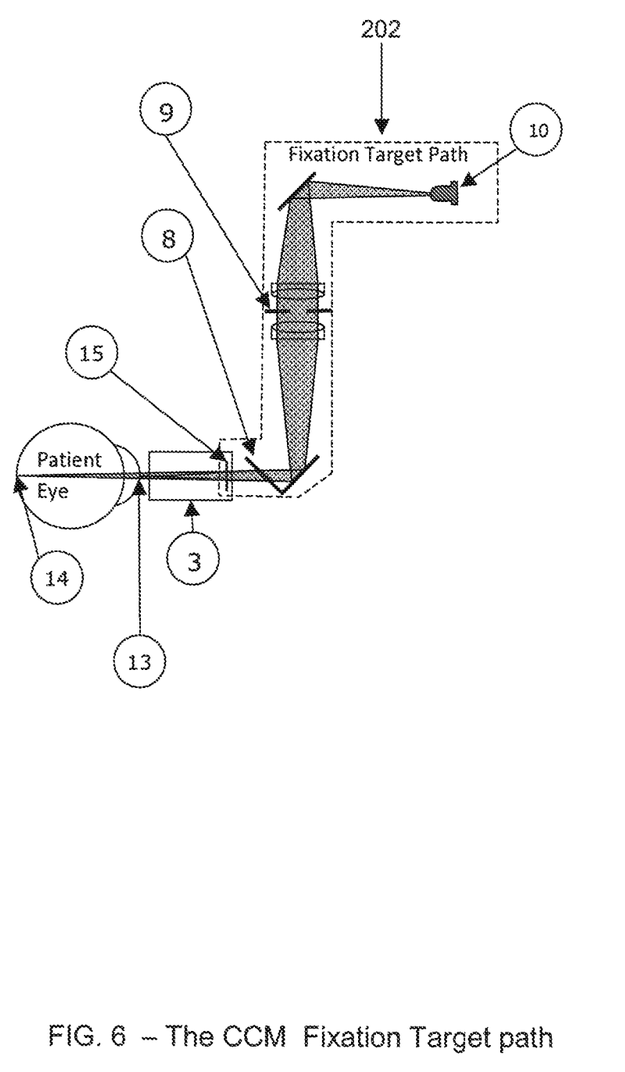
FIG. 6 shows a variation of a fixation target path of the corneal confocal microscope system.

FIG. 6 illustrates a representation of a fixation target path 202. The fixation target path 202 can be formed by a light source 10 (e.g., a high powered LED, or other sources with a wavelength different from the illumination light source 5—for example, red), and a target aperture 9 (e.g., having a particular shape such as a cross). This image has at least two purposes: the former is to provide a fixation mire focused on the retina 14 of the examined eye; the latter is to project an image (e.g., a cross) focused on the corneal surface 13 when the instrument is located at a distance away from the subject's eye. This latter aspect can be useful for an automatic alignment of the instrument. Moreover, the mirror 8 must be totally reflective in the illumination source wavelength (which is blue in this embodiment) and partially reflective in the fixation light source wavelength (which is red in this embodiment)

Figure 7A:
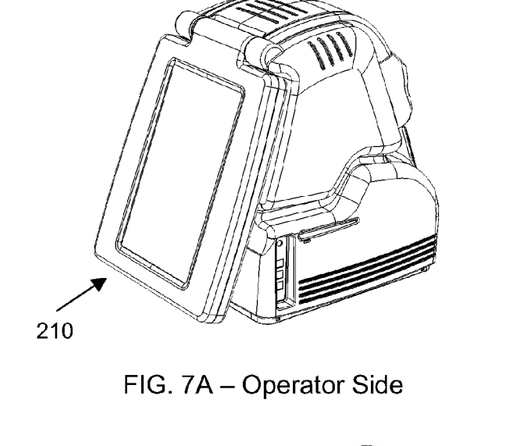
FIGS. 7A to 7E illustrate an example variation of the device as housed.
Figure 7B:
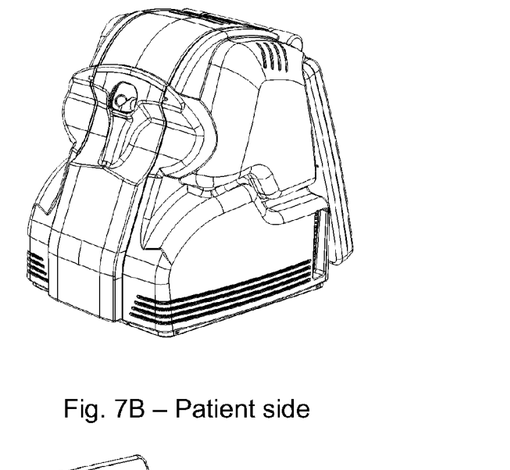
Figure 7C:
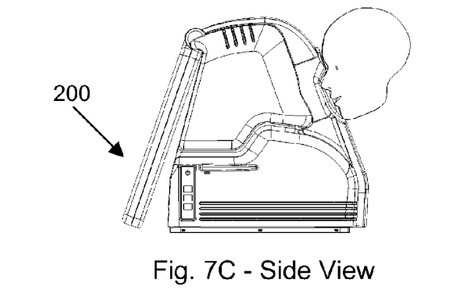
Figure 7D:
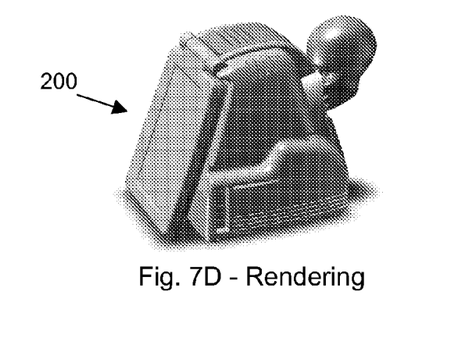
Figure 7E:
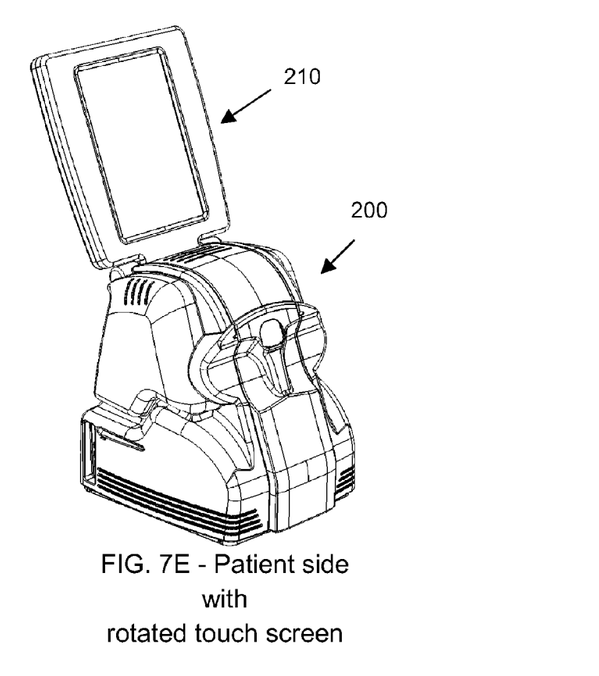

FIGS. 7A to 7E illustrate an example of the device as housed. FIG. 7A illustrates the operator or physician side interface 210 of the system 200. FIG. 7B illustrates the patient side where a patient can place an eye adjacent to the device without having the eye got in contact with the device 200. FIG. 7C illustrates a side view of the system 200 more clearly showing the patient's eye being spaced from the system's 200 housing. FIG. 7D illustrates a rendering of the system housing of FIG. 7A. FIG. 7E shows a variation of a system 200 where the operator side interface 210 can be pivoted or rotated towards a patient side of the system 200.

In addition, the system's housing can be adjustable to accommodate patient's that require adjustments of their posture or help in opening their eyelids.

Figure 8A:
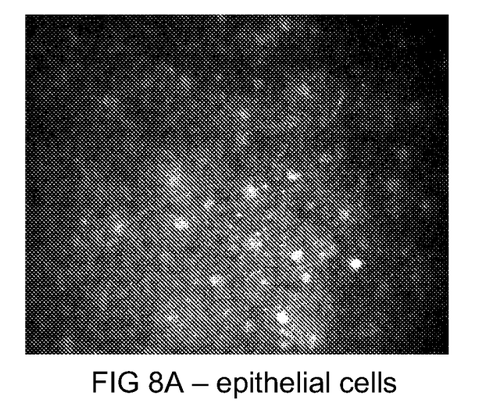
FIGS. 8A to 8C show samples of corneal confocal microscope images.
Figure 8B:
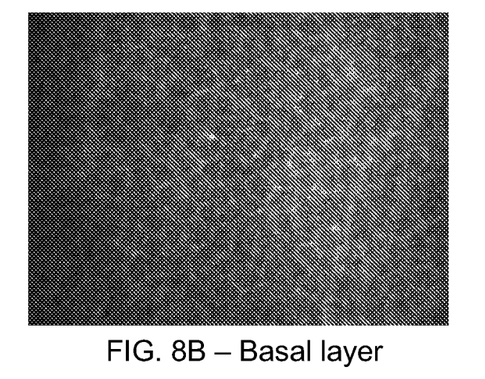
Figure 8C:
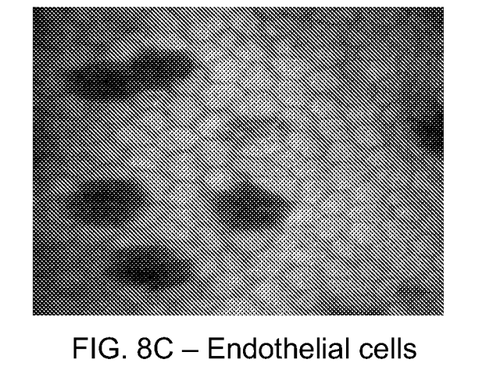

FIGS. 8A to 8C illustrate samples of corneal confocal microscope images. Including superficial cells of the corneal epithelium (FIG. 8A), the basal layer (FIG. 8B), and the deeper endothelium layer (FIG. 8C) usually used for cell count indexes.

Figure 9:
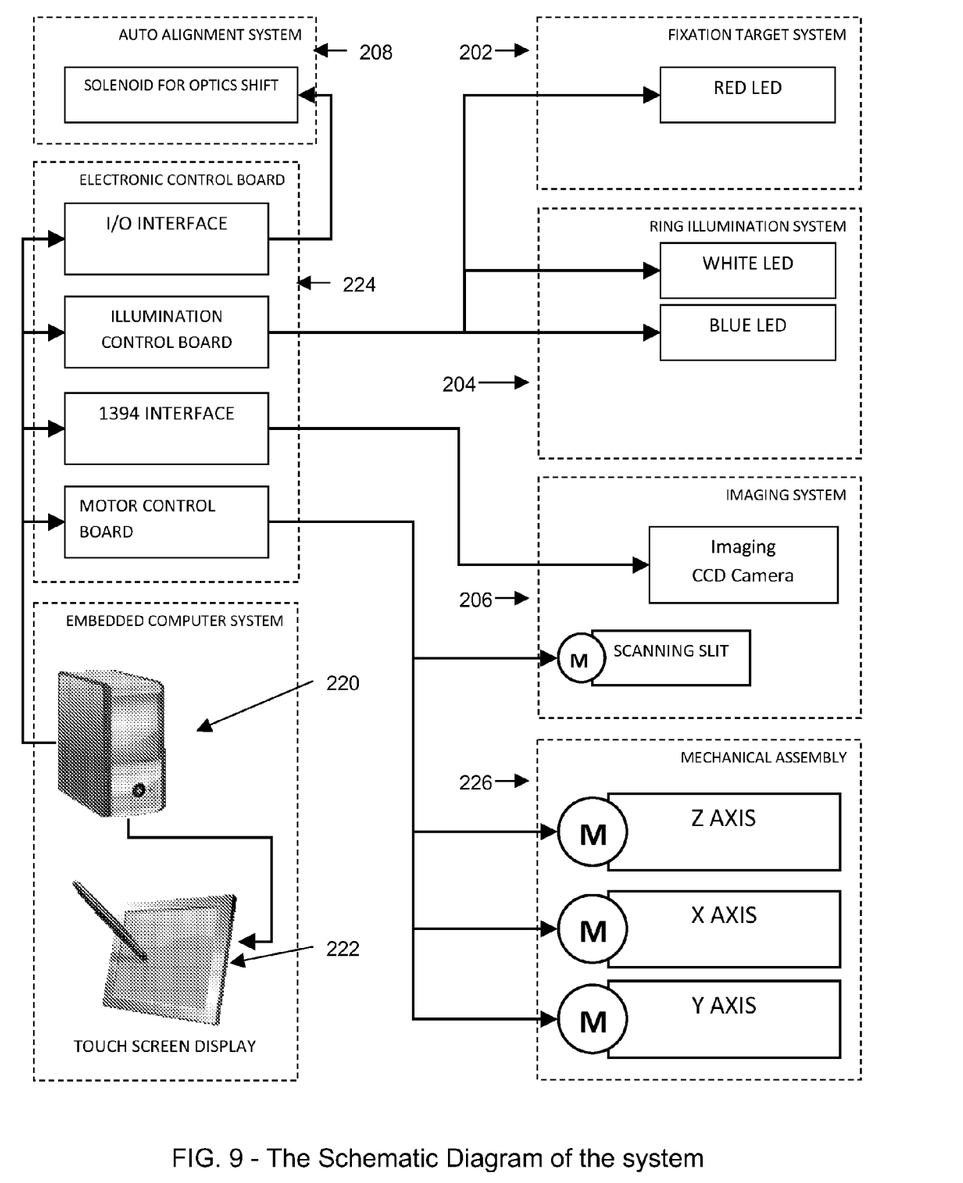
FIG. 9 provides a schematic diagram of a variation of a system according to the present disclosure.

FIG. 9 provides a schematic diagram of the functions of a system according to the present disclosure. As illustrated, a system can include a computer unit 220 having a touch screen 222 or other user interface. The computer unit 220 is coupled to an electronic control board 224 which is coupled to the fixation target system 202, ring illumination system 204, imaging system 206, auto-alignment system 208, and mechanical assembly 226.

Example of an Examination Method Using a Variation of a System Described 5 Herein:

Using the information coming from the computer analysis of the imaging system 206, the device aligns the mechanical assembly 226 optical axis perpendicularly to the corneal apex at the objective lens working distance. While in the alignment phase, the fixation target system 202 projects a cross pattern into the corneal surface, and the auto-alignment system 208 shifts into the imaging path in order to capture the non-confocal image that allows the system to be aligned at the corneal apex.

This precise alignment allows starting layer images capture automatically, without user intervention.

When perpendicularly aligned to the corneal apex, the mechanical assembly starts scanning toward the examined eye and acquiring images at 30 fps or more. These images can be stored on the computer system 220 or external storage. All images are then arranged into a volumetric rendering allowing for easy browsing among all the different layers. and accomplishing different types of analysis. Whenever a complete scan is captured, all images are analyzed and the corneal density indexes are calculated.

Finally the system can compute corneal pachimetry and compose a pachimetry profile by looking at the captured data of each single image.

The invention claimed is:

1. An ophthalmologic device for examining one or more corneal tissue layers of an eye of a patient comprising:
   a long working distance microscope objective lens;
   an illumination system having a drilled mirror conjugated to an entrance pupil of the objective lens to provide an annular illumination on the eye of the patient;
   a pupil reimager to conjugate the drilled mirror to the entrance pupil of the objective lens;
   a coaxial fixation target system configured to project a fixation target on a corneal surface of the eye of the patient;
   an autoalignment system that images the fixation target, the autoalignment system moveable between a first position outside of an image path and a second position in the image path to transform the ophthalmological device from a confocal to a non confocal operating mode.

2. The ophthalmologic device of claim 1 wherein the autoalignment system is removed from the imaging path to transform the ophthalmological device to a confocal microscope.

3. The ophthalmologic device of claim 2 wherein one or more aperture are conjugated with an illumination and an image plane to provide confocality.

4. The ophthalmologic device of claim 1, further comprising:
   a computer configured for controlling the autoalignment system; and a three-axis mechanical moveable assembly coupled to the autoalignment system and configured for aligning the eye with an optical axis of the device.

5. The ophthalmological device of claim 4, further comprising an image capture device, the three-axis mechanical moveable assembly being configured to shift the auto alignment system into the image path for allowing the image capture device to scan and acquire images along the optical axis inside the corneal tissue.

6. The ophthalmologic device of claim 1, further comprising an image capture device.

7. The ophthalmologic device of claim 6 wherein the image device comprises a CCD camera.

8. The ophthalmologic device of claim 1 wherein the pupil reimager comprises one or more reflective optical components.

9. The ophthalmologic device of claim 8 wherein the one or more reflective optical components comprise spherical mirrors.

10. A method for imaging one or more corneal tissue layers of an eye of a patient using an ophthalmologic device, the method comprising:
    projecting a fixation target on a cornea of the eye of the patient;
    capturing the projected fixation target coaxially with an imaging path of a confocal microscope by shifting a non confocal imaging device into the imaging path;
    matching a corneal apex of the eye of the patient at a microscope objective lens working distance by adjusting a three-axis mechanical assembly using an analysis of the captured fixation target image;
    transforming the ophthalmological device to a confocal operating mode by removing the non confocal imaging device from the imaging path;

illuminating the eye with an annular illumination provided by a light source projected onto a drilled mirror conjugated to an entrance pupil of the microscope objective lens;

acquiring one or more images of the one or more corneal tissue layers in the confocal operating mode using one or more confocal apertures;

collecting a set of bidimensional confocal images of the cornea by shifting the ophthalmological device to a new position along an optical axis and labeling each image in the set of images with depth information; and computing and displaying a 3 dimensional representation of the acquired corneal tissue layers.

\* \* \* \* \*